(12) United States Patent
Palmer et al.

(10) Patent No.: US 9,078,664 B2
(45) Date of Patent: Jul. 14, 2015

(54) BIPOLAR SURGICAL INSTRUMENT WITH TWO HALF TUBE ELECTRODES

(75) Inventors: Allen C. Palmer, Arlington, TN (US); Kevin C. Edwards, Olive Branch, MS (US)

(73) Assignee: GYRUS ACMI, INC., Southborough, MA (US)

( * ) Notice: Subject to any disclaimer, the term of this patent is extended or adjusted under 35 U.S.C. 154(b) by 446 days.

(21) Appl. No.: 13/528,252

(22) Filed: Jun. 20, 2012

(65) Prior Publication Data

US 2013/0345704 A1 Dec. 26, 2013

(51) Int. Cl.
*A61B 18/14* (2006.01)
*A61B 18/00* (2006.01)

(52) U.S. Cl.
CPC ..... *A61B 18/148* (2013.01); *A61B 2018/00083* (2013.01); *A61B 2018/00208* (2013.01); *A61B 2018/00595* (2013.01); *A61B 2018/00601* (2013.01)

(58) Field of Classification Search
CPC .......... A61B 2018/00601; A61B 2018/00589; A61B 2018/00607; A61B 17/32; A61B 18/1482; A61B 2018/126; A61B 2018/00148; A61B 18/148
USPC ........ 606/50, 34, 41; 600/104, 112, 121, 127, 600/136
See application file for complete search history.

(56) References Cited

U.S. PATENT DOCUMENTS

| | | | |
|---|---|---|---|
| 4,646,738 A | 3/1987 | Trott | |
| 5,290,282 A | 3/1994 | Casscells | |
| 5,364,395 A | 11/1994 | West, Jr. | |
| 5,707,350 A | 1/1998 | Krause et al. | |
| 5,810,809 A | 9/1998 | Rydell | |
| 5,904,681 A * | 5/1999 | West, Jr. | 606/41 |
| 6,193,715 B1 | 2/2001 | Wrublewski et al. | |
| 6,827,725 B2 | 12/2004 | Batchelor et al. | |
| 7,052,494 B2 | 5/2006 | Goble et al. | |
| 7,150,747 B1 | 12/2006 | McDonald et al. | |
| 7,247,161 B2 | 7/2007 | Johnston et al. | |
| 7,318,831 B2 | 1/2008 | Alvarez et al. | |
| 2006/0178670 A1 | 8/2006 | Woloszko et al. | |
| 2010/0082026 A1* | 4/2010 | Curtis | 606/33 |
| 2010/0121321 A1 | 5/2010 | Ryan | |

FOREIGN PATENT DOCUMENTS

WO WO 99/37225 7/1999

OTHER PUBLICATIONS

Jul. 26, 2013 International Search Report and Written Opinion issued in International Patent Application No. PCT/US2013/039823.

* cited by examiner

*Primary Examiner* — Catherine Voorhees
(74) *Attorney, Agent, or Firm* — Oliff PLC

(57) ABSTRACT

A surgical instrument includes a hollow tubular member having a closed distal working end, a proximal end and an outer surface, with an opening in a side wall at or adjacent the distal working end. The instrument includes a first electrical insulation layer disposed on at least part of the outer surface of the hollow tubular member, a first electrode disposed on an outer surface of the first electrical insulation layer, and a second electrode disposed on the outer surface of the first electrical insulation layer. The first and second electrodes are electrically isolated from each other, and each includes an active segment and an inactive segment. The active segments of the first and second electrodes are disposed respectively on opposing sides of the hollow tubular member preferably within about 3.0 mm of the opening in the side wall of the hollow tubular member.

20 Claims, 11 Drawing Sheets

BIPOLAR SURGICAL INSTRUMENT WITH TWO HALF TUBE ELECTRODES

BACKGROUND

This disclosure relates to surgical instruments, and in particular to surgical cutting instruments having two electrodes for providing coagulation and/or vaporization of tissue.

Surgical apparatus used to shave, cut, resect, abrade and/or remove tissue, bone and/or other bodily materials are known. Such surgical apparatus can include a cutting surface, such as a rotating blade disposed on an elongated inner tube that is rotated within an elongated outer tube having a cutting window. The inner and outer tubes together form a surgical cutting instrument or unit. In general, the elongated outer tube includes a distal end defining an opening or cutting window disposed at a side of the distal end of the outer tube. The cutting window of the outer tube exposes the cutting surface of the inner tube (typically located at a side of the distal end of the inner tube) to tissue, bone and/or any other bodily materials to be removed. A powered handpiece is used to rotate the inner tube with respect to the outer tube while an outer tube hub (connected to the proximal end of the outer tube) is fixed to the handpiece and an inner tube hub (connected to the proximal end of the inner tube) is loosely held by the powered handpiece and is rotated by a motor of the handpiece.

In some instruments, the inner tube is hollow and has a cutting window on a side surface of its distal end such that tissue, bone, etc., will be cut or shaved as the cutting window of the inner tube aligns with and then becomes misaligned with the cutting window of the outer tube as the inner tube is rotated within the outer tube. In this regard, it can be said that the cutting device nibbles or takes away small pieces of the bone, tissue, etc., as the inner tube is rotated within the outer tube.

In some instruments, a vacuum is applied through the inner tube such that the bodily material that is to be cut, shaved, etc., is drawn into the windows of the inner and outer tubes when those windows become aligned, thereby facilitating the cutting, shaving, etc., of the tissue, which then travels through the inner tube due to the suction. It also is common to supply an irrigation fluid, which can include a liquid, to the surgical site via a passage provided between the inner and outer tubes.

Microdebrider shaver blades are common instruments used in endoscopic surgery. The shaver blade delivers high speed mechanical cutting of tissue at a specified area of anatomy that the surgeon can reach through a minimally invasive incision or natural orifice. One challenge during procedures using such instruments can be the slowing down or stopping of bleeding (hemostasis) during the procedure. One solution for maintaining proper hemostasis during a procedure is to utilize an electrocautery instrument that can be used inside the same minimally invasive surgical corridor. In a minimally invasive procedure, every time the surgeon exchanges the cutting instrument for the electrocautery instrument there is a corresponding increase in the time required to perform the procedure and there is a risk of traumatizing the anatomy due to the exchange of the instruments. Thus, it is convenient to combine the mechanical cutting and electrocautery instruments to form one instrument performing both functions. By providing a microdebrider shaver blade that also can perform electrocautery, the need to perform tool exchanges at the surgical site is reduced and can even be eliminated.

There are two standard types of electrocautery: bipolar and monopolar. Monopolar cautery uses one electrode at the surgical site and then relies on a neutral electrode placed somewhere else on the patient (typically on the skin of the patient) to help disperse the energy enough to pass the energy safely through the patient. Bipolar cautery does not use a separate neutral electrode. Instead, bipolar cautery delivers the energy and returns the energy through the device using two electrodes at the surgical site. That is, a bipolar device will provide two electrodes at the surgical site, one active electrode and one return electrode.

For typical sinus surgery, the bipolar electrode is preferred due to the close proximity of critical anatomy to the typical surgery sites in the sinuses. That is, a bipolar device enables the energy to be applied at a more focused location.

It is known to provide microdebrider shaver blades with bipolar energy electrodes. The bipolar shaver blades utilize a series of overlapping layers to provide the two electrodes needed to transfer energy into the tissue at the surgical site to achieve coagulation. In the known structure, two concentric electrically conductive layers are electrically isolated from each other in order to establish the two isolated electrodes used for bipolar cautery. An example of such a known structure is shown in FIG. 1. The FIG. 1 microdebrider includes a stationary outer tubular member 110 and a rotatable inner tubular member 130 that rotates within the outer tubular member 110. The outer tubular member 110 includes a sideward-facing opening at its distal end which has multiple cutting teeth 112 so as to form a cutting window at the distal end of the outer tubular member 110. The inner, rotatable tubular member (cutting member) 130 also includes a sideward-facing opening having multiple cutting teeth 132. As is known, cutting or shaving takes place by rotating the inner tubular member 130 within the outer tubular member 110 while applying suction through the tubular member 130. In addition, irrigation fluid can be provided to the surgical site through a gap that is formed between the outer tubular member 110 and the inner tubular member 130. In the FIG. 1 cauterizing microdebrider, the outer tubular member 110 is electrically conductive and forms one of the two electrodes of the bipolar electrocautery instrument. An electrically insulative film 115 covers most of the outer surface of the stationary, outer tubular member 110 so that only the teeth 112 and a narrow strip at the distal-most tip of the outer tubular member 110 are not covered by the insulating film 115. The narrow strip at the distal-most tip defines one of the electrodes (for example, the active electrode). An electrically conductive layer or film 120 is formed over part of the insulating film 115. The electrically conductive layer 120 (also called a sheath) forms the second electrode (for example, the return electrode) of the bipolar electrocautery instrument. An outermost electrically insulating layer or film 140 is then formed over most of the instrument except for the distal end thereof so that the electrically conductive layer 120 is exposed only at the distal end of the instrument.

The known design shown in FIG. 1 results in a horseshoe-shaped area of the electrically insulating film 115 being present between the two electrodes formed by the tip of the outer tubular member 110 and the distal end of the electrically conductive layer 120. This design restricts (limits) the separation distance that is possible between the two electrodes (the electrode formed at the tip of member 110 and the electrode formed by layer 120) in that it becomes more difficult to obtain good contact between the tissue and each electrode as one increases the separation between the two different layers which form the two electrodes. In other words, because the electrode formed by the tip of tubular member 110 is recessed compared to the electrode formed by layer 120, it can be difficult to cause both electrodes to contact the tissue that is to be cauterized. In addition, because the electrode formed by layer 120 surrounds the electrode formed at the tip of member 110, it can be difficult to place the electrodes (one of which is an active electrode and the other of which is a return electrode) on opposite sides of the tissue that is to be cauterized.

SUMMARY

In view of the foregoing, it is desirable to provide a bipolar surgical instrument with an improved electrode structure. By providing both electrodes (an active electrode and a return electrode) in the same layer, it can be easier to contact the electrodes with the tissue that is to be cauterized. Such an arrangement also can make it easier to place the electrodes at the appropriate positions on opposite sides of the area that is to be cauterized.

According to some embodiments, a surgical instrument includes a hollow tubular member having a closed distal working end, a proximal end and an outer surface, with an opening in a side wall at or adjacent the distal working end. The instrument includes a first electrical insulation layer disposed on at least part of the outer surface of the hollow tubular member. A first electrode is disposed on an outer surface of the first electrical insulation layer, and a second electrode is disposed on the outer surface of the first electrical insulation layer. The first and second electrodes are electrically isolated from each other. The first electrode includes a first active segment and a first inactive segment. The second electrode includes a second active segment and a second inactive segment. The first and second active segments are disposed respectively on opposing sides of the hollow tubular member preferably within about 3.0 mm of the opening in the side wall of the hollow tubular member.

Such an arrangement enables the two electrodes to be easily contacted with the tissue that is to be cauterized and thus makes it easier to cause the cauterizing energy to flow through the tissue because it is easier to place the active and return electrodes on opposite sides of the tissue area to be cauterized.

In accordance with some embodiments, the first and second active segments are disposed respectively within 1.0 mm of the opening in the side wall of the hollow tubular member.

In accordance with some embodiments, one or both of the first and second active segments are further disposed at least partially into a segment of the closed distal working end of the hollow tubular member.

In accordance with some embodiments, the surgical instrument is a cutting instrument and includes a rotatable cutting member disposed within the hollow tubular member. However, other cutting arrangements are possible. For example, the cutting member can reciprocate axially within the hollow tubular member.

In accordance with some embodiments, a second electrical insulation layer is disposed at least partially over the outer surface of the hollow tubular member, the first and second inactive segments of the first and second electrodes, or both. In addition, the first electrical insulation layer, the second electrical insulation layer, or both can include geometric features (for example protrusions) adapted to isolate the first and second electrodes. Furthermore, an outer sheath can be disposed at least partially over the second electrical insulation layer.

In accordance with some embodiments, the first active segment, the second active segment, or both include a forward facing projection. The projection(s) is/are easier to place on opposite sides of the tissue that is to be subjected to coagulation.

In accordance with some embodiments, at least a portion of the side wall at the opening is electrically conductive and can function as an active electrode segment. Such an arrangement can be used to apply a signal appropriate for vaporizing tissue by using the hollow tubular member as one electrode (for example, the active electrode) and by using one or both of the first and second electrodes as a return electrode.

Another aspect of the invention relates to a bipolar surgical cutting instrument. In accordance with one embodiment, the bipolar surgical cutting instrument includes an electrically conductive hollow tubular member having a closed distal working end, a proximal end and an outer surface, with an opening in a side wall at or adjacent the distal working end. The cutting instrument also includes a rotatable cutting member disposed within the electrically conductive hollow tubular member. A first electrical insulation layer is disposed on at least part of the outer surface of the electrically conductive hollow tubular member. A first electrode is disposed on an outer surface of the first electrical insulation layer, and a second electrode is disposed on the outer surface of the first electrical insulation layer. The first and second electrodes are electrically isolated from each other. The first electrode includes a first active segment and a first inactive segment. The second electrode includes a second active segment and a second inactive segment. The first and second active segments are disposed respectively on opposing sides of the electrically conductive hollow tubular member preferably within about 2.0 mm of the opening in the side wall of the electrically conductive hollow tubular member.

In accordance with preferred embodiments, the rotatable cutting member of the surgical cutting instrument is a second hollow tubular member through which suction can be applied to remove tissue that has been resected from the surgical site. In addition, it is preferable that the surgical cutting instrument includes a second electrical insulation layer disposed at least partially over the outer surface of the electrically conductive hollow tubular member, the first and second inactive segments of the first and second electrodes, or both. According to a preferred embodiment, the first electrical insulation layer, the second electrical insulation layer, or both include geometric features (for example, protrusions) adapted to isolate the first and second electrodes.

BRIEF DESCRIPTION OF THE DRAWINGS

Various exemplary embodiments of the disclosed surgical instrument will be described in detail with reference to the following drawings in which.

DETAILED DESCRIPTION OF EMBODIMENTS

The following exemplary embodiments are described below with reference to the figures in the context of human surgery, such as ear, nose and throat surgery, and in particular sinus surgery as well as head and neck surgery. The following exemplary embodiments may also be utilized in spinal surgery, orthopedic surgery, and various other surgical applications. All exemplary embodiments of the invention are intended to be used in any applicable field of endeavor.

Figure 2:
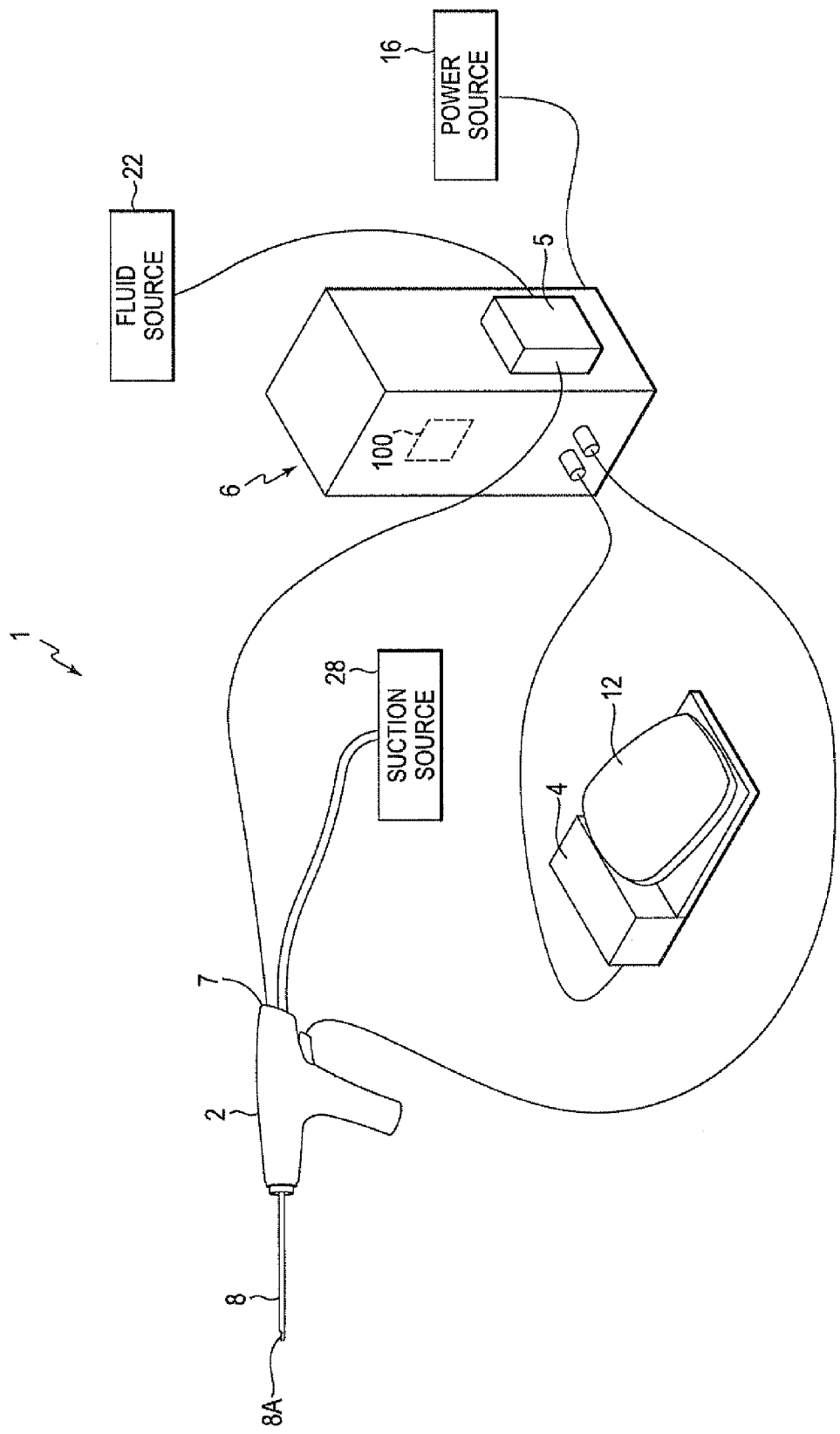
FIG. 2 illustrates a perspective view of a powered surgical instrument system that incorporates a surgical instrument, control unit, fluid source and suction source.

FIG. 2 is a schematic of a powered surgical instrument system. Except for the first and second electrodes, to be described hereafter, the system may be in accordance with the system described in U.S. Pat. No. 7,247,161, the disclosure of which is incorporated herein by reference in its entirety. Examples of other systems to which the invention is applicable are described in U.S. Pat. No. 7,318,831, U.S. Pat. No. 7,052,494 and U.S. Pat. No. 6,827,725, the disclosures of which are incorporated herein by reference in their entireties. As shown in FIG. 2, the powered surgical instrument system 1 includes a handle (or handpiece) 2, a footswitch 4 (with pedal 12), fluid (liquid and/or gas) source 22, suction source 28, a control unit 6, fluid pump 5 and a fluid inlet/irrigation outlet 7. The system is supplied with power from a power source 16 such as a wall outlet. The suction source 28 may be an external suction source such as provided by attachment to a facility suction outlet provided on a wall. The handpiece 2 is connected, at its distal end, to a surgical instrument 8. The surgical instrument 8 in this embodiment includes a cutting tip at its distal working end 8A that is used, for example, to cut, shave, remove, resect and/or abrade tissue, bone and/or other bodily materials.

Figure 3:
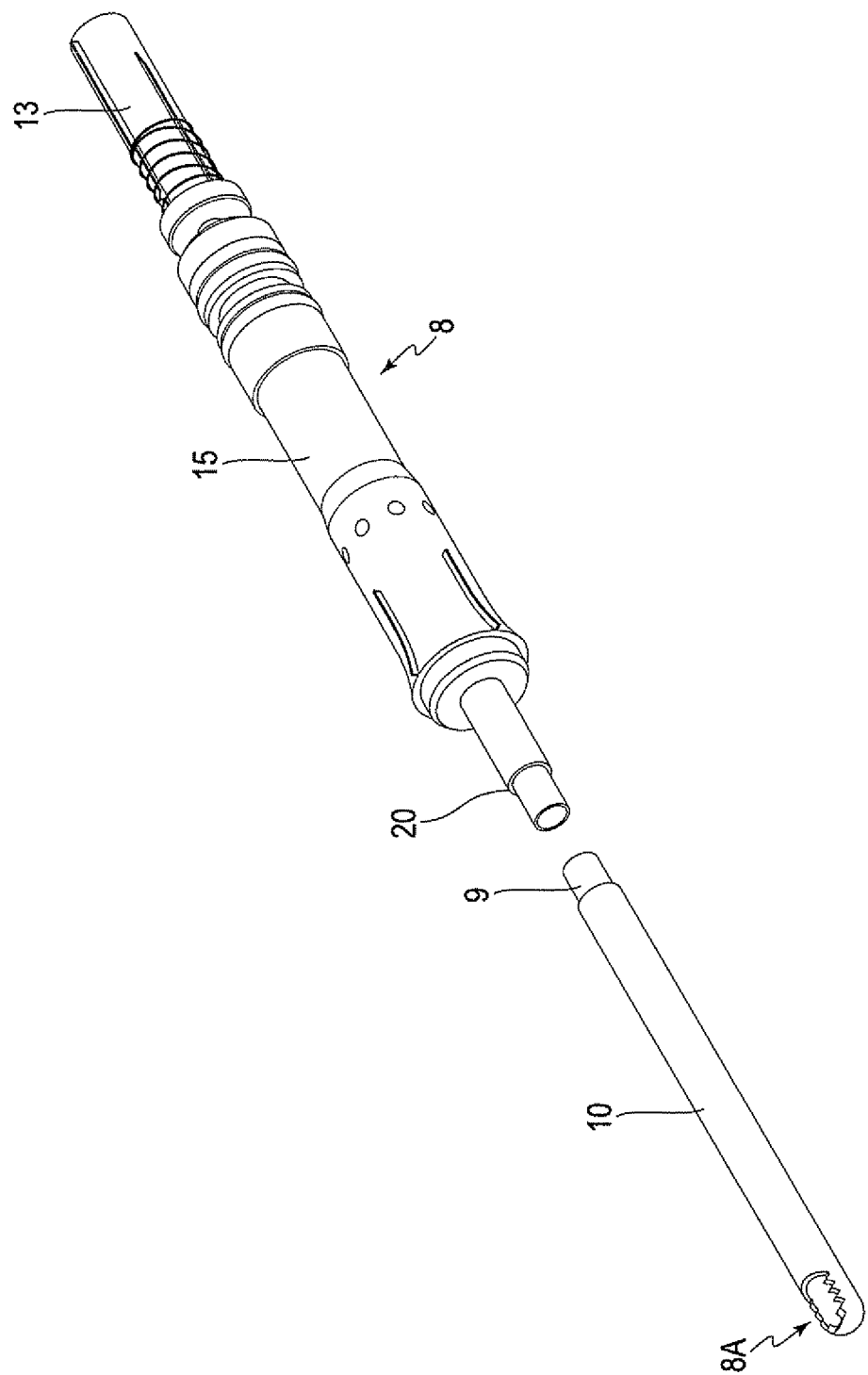
FIG. 3 is a perspective view of an exemplary embodiment of a surgical instrument in accordance with the present disclosure.

FIG. 3 illustrates a perspective view of an exemplary embodiment of the surgical instrument 8. The instrument 8 incorporates an inner tube 9 and an outer tube 10. In this exemplary embodiment, an inner tube hub 13 is formed on the second end 14 (see FIG. 4) of the inner tube 9 and an outer tube hub 15 is formed on the second end 17 (see FIG. 4) of the outer tube 10. For purposes of this disclosure, each tube 9/10 and its hub 13/15 are collectively referred to as a "tube" or "member." The inner tube 9 is inserted into a fluid passage 20 formed within the outer tube 10 so that the inner tube 9 is co-axially disposed within the outer tube 10 until the external distal tip of the inner tube 9 contacts the internal distal surface of the outer tube 10. The outer tube 10 has a larger diameter than the inner tube 9, thus allowing for insertion of the inner tube 9 within the outer tube 10. However, it should be appreciated that the inner and outer tubes will be pre-assembled prior to delivery to the customer. Thus, a customer will most likely not be inserting the inner tube into the outer tube. Irrigation liquid can be supplied to the surgical site by supplying the liquid to the passage 20 via an inlet 26.

The inner and outer tube hubs 13, 15 couple the inner and outer tubes 9, 10, respectively, to the handpiece 2. Once coupled to the handpiece 2, the outer tube 10 will be fixed relative to the handpiece 2 (but may be manually rotated to change rotational position of the cutting window as is known), but the inner tube 9 will be rotatable relative to the outer tube 10 and the handpiece 2.

Figure 4:
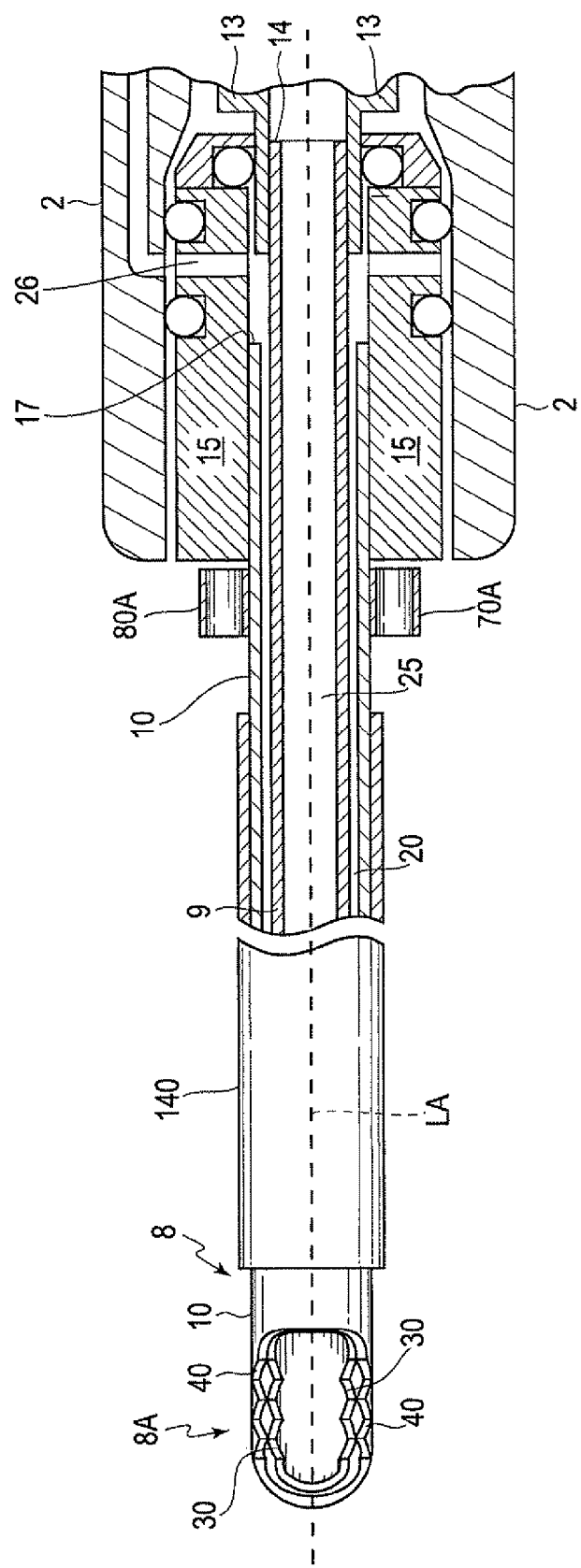
FIG. 4 is a side view, partially in cross-section, of a surgical instrument in accordance with an embodiment of the present disclosure.
Figure 5:
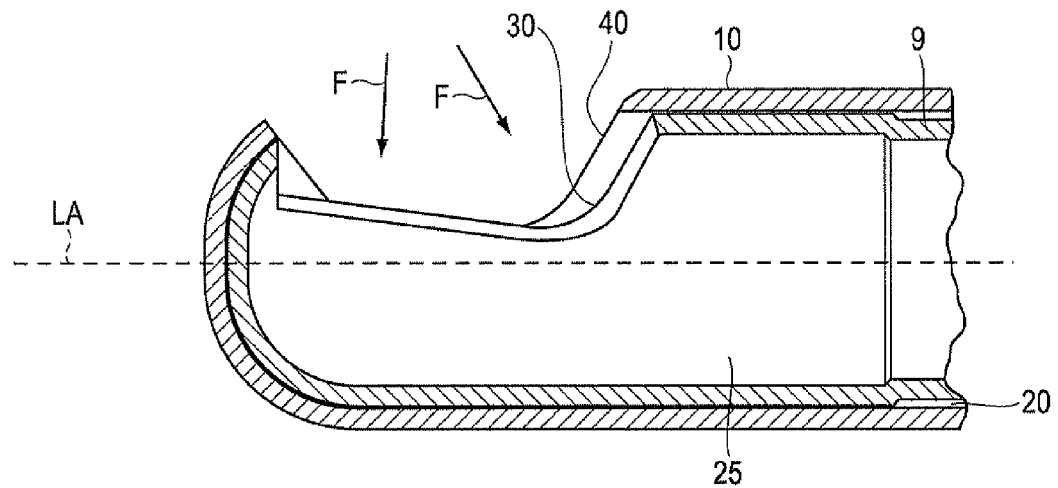
FIG. 5 is a side, cross-sectional view of the FIG. 4 surgical instrument distal tip with the cutting windows being in complete alignment.
Figure 6:
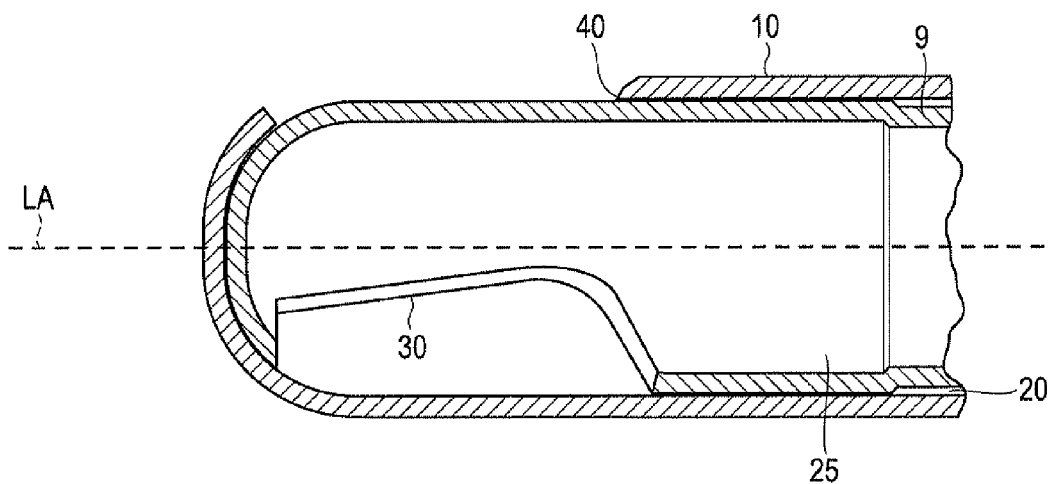
FIG. 6 is a side, cross-sectional view similar to FIG. 5, but with the cutting windows being in complete mis-alignment so that suction is not applied through the cutting windows.

Referring to FIG. 4, which shows a perspective view of the tip 8A and a cross-sectional view of the handpiece 2 and proximal ends of the tubes 9 and 10, the outer tube 10 includes a cutting window 40 disposed at a side of its distal working end. Thus, the outer tube 10 can be referred to as a first cutting blade. The inner tube 9 also includes a cutting window 30 disposed at a side of its distal end. Thus, the inner tube 9 can be referred to as a second cutting blade. The edges of the cutting windows 30 and 40 can be serrated, smooth or a combination of serrated and smooth to form cutting surfaces. As mentioned previously, the inner tube 9 rotates within the outer tube 10, and thus as the inner tube 9 rotates, the cutting windows 30 and 40 become aligned with each other as shown in FIG. 5 and then become misaligned with each other as shown in FIG. 6. When the cutting windows 30 and 40 are misaligned with each other as shown in FIG. 6, the side of the inner tube 9 distal tip opposite from the cutting window 30 blocks the cutting window 40 of the outer tube 10.

The first, or outer cutting blade (outer tube 10) thus is an outer tube having a proximal end and a distal end, with a cutting window 40 disposed in a side wall of the outer tube 10 near (adjacent) the distal end.

The inner, second cutting blade (inner tube 9) is a tubular body having a proximal end and a distal end, with cutting window 30 disposed at a side of its distal end. As mentioned previously, the inner tube 9 is rotatably disposed inside of the outer tube 10 such that the surgical instrument 8 cuts tissue by rotating the inner tube 9 within the outer tube 10 while a vacuum is applied through an internal bore 25 of the inner tube 9 to draw the tissue into the cutting windows 30 and 40 of the tubes 9 and 10 and sever the tissue by rotation of the inner tube 9. Thus, the inner tube 9 is an inner rotating member having a cutting member near its distal end. The inner rotating member need not be a tube. For example, the inner rotating member could be a shaft with a cutting member at its distal end. With such an arrangement, suction would be applied through the hollow outer tube 10.

FIG. 4 also illustrates electrical connections 80A and 70A provided for each of the electrodes 80 and 70. Connections 70A and 80A are electrically conductive (metallic) hollow connectors that can be connected to signal supply/return lines (not shown). Connection 80A is attached to the proximal end of electrode 80, and connection 70A is attached to the proximal end of electrode 70.

Thus, once the surgical instrument 8 is coupled with the handpiece 2 and the signal/return lines are attached to the connections 70A and 80A, suction can be applied through the internal bore 25 of the inner tube 9, irrigation fluid can be supplied through passage 20 between the inner tube 9 and the outer tube 10 via the inlet 26, and an appropriately modulated RF signal can be supplied to one of the electrodes at the distal tip of the outer tube 10 via, for example, connection 80A (assuming that the electrode 80 connected to connection 80A is the active electrode), while energy is received through connection 70A (assuming that the electrode 70 connected to connection 70A is the return electrode).

Figure 7:
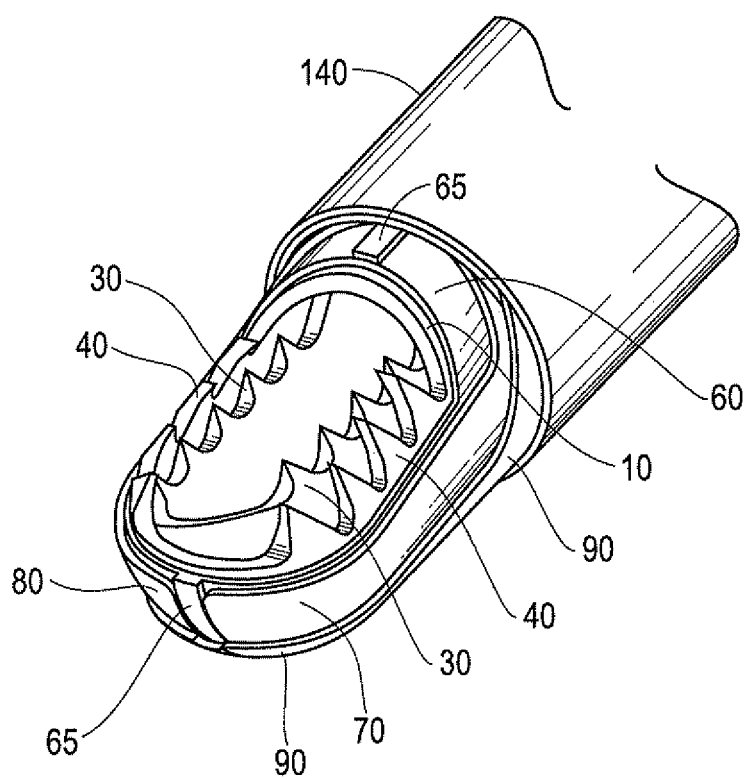
FIG. 7 is a perspective view of the distal tip of a bipolar surgical instrument according to one embodiment.

An exemplary structure for the first and second electrodes in accordance with an embodiment of the invention will now be described in connection with FIGS. 7-10. FIG. 7 is a perspective view of the distal working end of the surgical instrument 8 shown in FIG. 4. In FIG. 7, the inner tube 9 is rotated relative to the outer tube 10 so that the cutting window 30 of the inner tube 9 is slightly misaligned with the outer cutting window 40 of the outer tube 10. In the FIG. 7 embodiment, the outer tube 10 is made from stainless steel and is electrically conductive. Accordingly, an electrically insulative film layer 60 (first electrical insulation layer) is formed over the outer surface of the outer tube 10. A first electrode 70 is formed on a first side of outer tube 10 and is electrically isolated from the tube 10 by the insulative layer 60. A second electrode 80 is formed on a second side of the tube 10 opposite from the first side. Second electrode 80 also is electrically isolated from the outer tube 10 by the insulative layer 60. The first and second electrodes 70 and 80 are physically separated from each other, and thus one of the electrodes (for example, first electrode 70) can function as the active electrode whereas the other electrode (for example, second electrode 80) can function as the return electrode.

In the FIG. 7 embodiment, the electrically insulative layer 60 includes a geometric feature such as a longitudinally extending central protrusion 65 that is formed between the first and second electrodes 70 and 80 so as to improve the electrical isolation of those two electrodes from each other. In one embodiment, the protrusion 65 has a height that is substantially the same as the thickness of the electrically conductive layers forming the electrodes 70 and 80. A further electrically insulative layer 90 (second electrical insulation layer) is formed over the first and second electrodes. The electrically insulative layer 90 defines the active regions or areas of the electrodes 70 and 80 that can be exposed to tissue during use. The portions of the electrodes 70 and 80 covered by the layer 90 can be referred to as the inactive regions or areas of the electrodes. Furthermore, a sheath 140 can be provided over all but the distal tip section of the surgical instrument 8. Portions of the electrodes 70 and 80 covered by the sheath 140 also are considered as the inactive regions of the electrodes.

Figure 8:
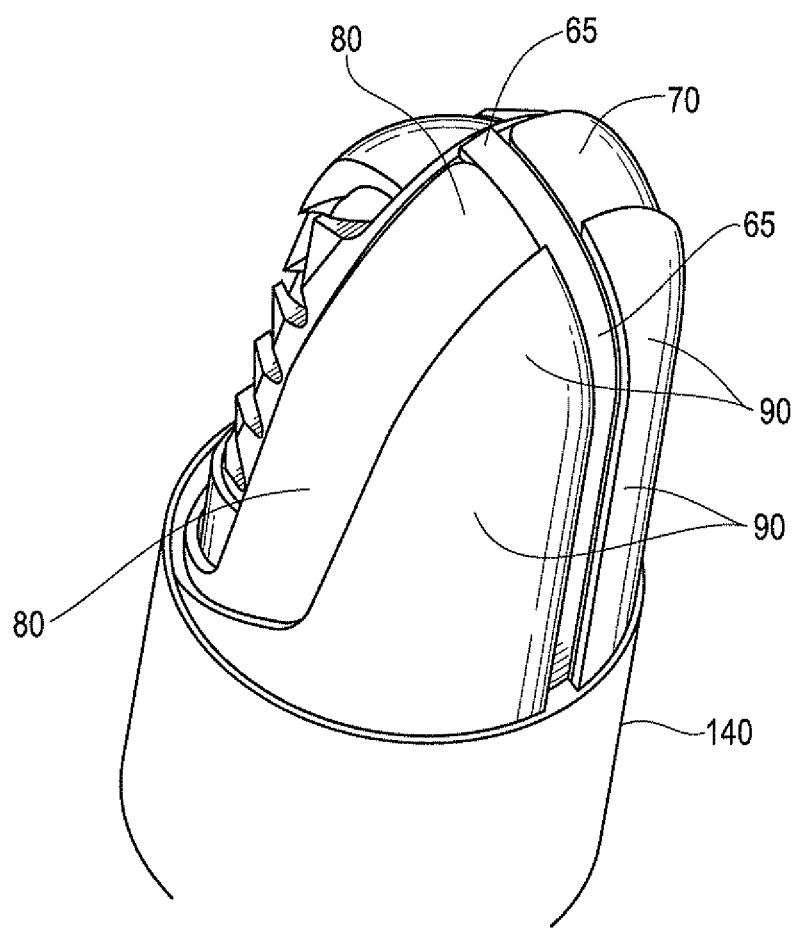
FIG. 8 is a perspective view of the FIG. 7 bipolar surgical instrument from a different view point.

FIG. 8 is a perspective view of the rear side of the FIG. 7 surgical instrument and more clearly shows the insulative layer 90. It can be appreciated from FIGS. 7 and 8 that the active regions of the electrodes 70 and 80 are disposed on opposite sides of the cutting window 40 and extend distally onto the closed distal end of the outer tube 10. Although the insulative layer 90 does not overlap the protrusion 65 in FIGS. 7 and 8, the insulative layer could be a single layer that covers at least the portion of the protrusion 65 where the two insulative layers 90 are adjacent to each other in FIG. 8. However, it is preferable to provide the insulative layer 90 as two separate pieces so that each electrode 70, 80 can be formed with insulative layer 90 on it as separate units (see FIG. 10). Furthermore, a protrusion could extend inwardly from the insulative layer 90 if that layer overlapped the area between the electrodes 70 and 80.

Figure 9:
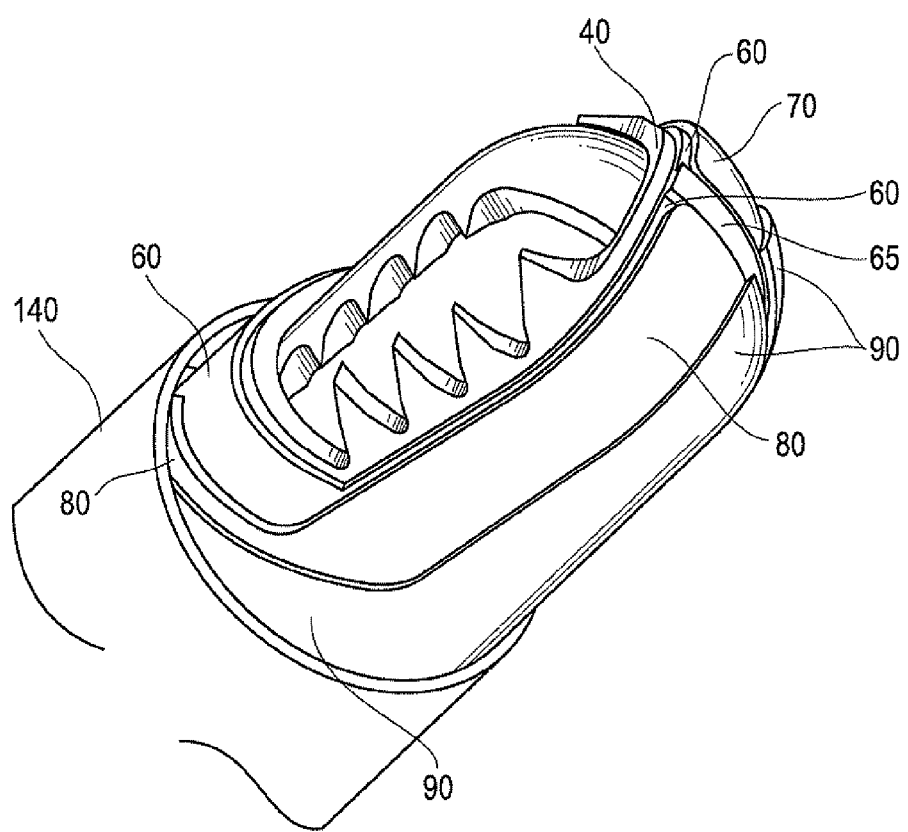
FIG. 9 is a perspective view of the FIG. 7 bipolar surgical instrument from another, different view point.

FIG. 9 is another perspective view of the distal tip of the surgical instrument shown in FIGS. 7 and 8. As can be seen more clearly in FIG. 9, the edge of each electrode 70, 80 that is adjacent to the cutting window 40 of the outer cutting tube 10 is recessed slightly so that a portion of the insulative layer 60 is exposed. This better ensures that the electrodes 70 and 80 are electrically isolated from the cutting tube 10 at the location of the cutting window 40, and prevents the edges of the electrodes 70 and 80 from being damaged by the cutting procedure. The electrodes 70 and 80 preferably are disposed within about 3.0 mm of the cutting window 40, and can be within 0.2 mm or even 1.0 mm of the cutting window 40. Preferably the electrodes 70 and 80 are spaced from the cutting window 40 by 0.5 mm to 1.0 mm to facilitate tissue contact with the electrodes 70 and 80. The range can be up to 2.0 mm while still achieving a very good cautery effect, although it can be more difficult to contact both electrodes 70 and 80 with the tissue.

Figure 10:
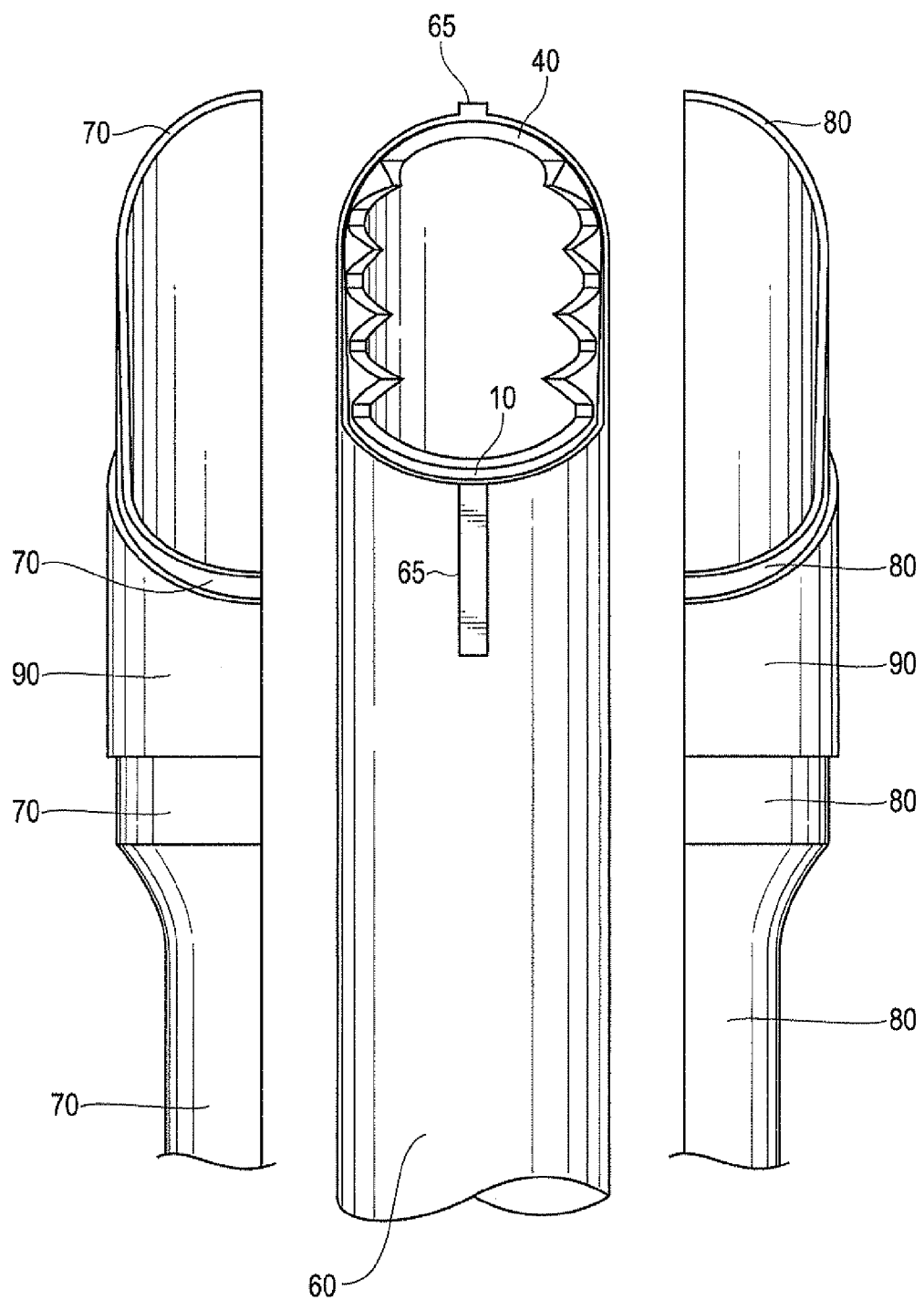
FIG. 10 is an exploded side view of the FIG. 7 bipolar surgical instrument with the two electrodes separated from the cutting blade portion of the surgical instrument.

FIG. 10 is an exploded view of the surgical instrument. Each electrode 70, 80 is formed as a separate piece and has insulative layer 90 formed on it. For example, electrode 70 is formed as a first half tube which covers a left half of the outer tube 10, whereas electrode 80 is formed as a second half tube which covers the right half of the outer tube 10. As mentioned previously, if the outer tube 10 is electrically conductive, then the outer tube 10 is covered with an electrically insulative layer 60, preferably having a geometric feature such as protrusion 65 at least at the distal tip portion thereof where the two electrodes 70 and 80 are exposed. The protrusion 65 can extend the length between the electrodes 70 and 80 to prevent undesired electrical conduction between the electrodes in the inactive sections. This would be most likely to occur when the cutting tip is covered with eschar, creating a less-resistive electrical path in the inactive portions. In this case, the cautery effect at the tip would be diminished or lost. Greater isolation in the inactive regions might also be accomplished by shaping the electrodes (cutting away material in the inactive zones) such that the electrodes are functionally adjacent to each other only at the distal exposed tip. The protrusion 65 extends along at least a portion of the axial length of the tubular member forming the outer tube 10. The more proximal ends of the electrodes 70 and 80 will be covered by the insulative sheath 140, and thus do not need to be covered with insulative layer 90. Furthermore, near the proximal end of the outer tube 10, electrodes 70 and 80 include electrical connections 70A and 80A respectively. Alternatively, the electrodes 70 and 80 could be formed only near the distal end of the outer tube 10, and signal/return lines could extend from connections 70A and 80A positioned near the hub 15 toward the distal end of the outer tube 10 where they attach to their corresponding electrodes 70 and 80.

The outer tube 10 would be coated, with the coating selectively (powder coat, insert-molding, vapor deposition are all acceptable methods) applied or removed post-coating to expose the desired region of tube 10 and form the raised protrusion 65. The coating thickness of layer 60 preferably is in the range of 0.005-0.015 inch thick, depending on the dielectric strength of the coating with respect to the insulative requirements of the device. The electrode thicknesses 70, 80 preferably are in the range of 0.005-0.010 inch. Thus, the thickness of protrusion 65 is desired to be equal to the thickness of electrodes 70, 80. Electrodes 70 and 80 may be formed from a steel tube similar to 10, coated similar to 10, and then split by an additional machining, laser or other operation. Electrodes 70 and 80 could also be formed individually by stamping or similar method and then coated. Electrodes 70 and 80 need not adhere to layer 60, but may be placed and held over layer 60 with manufacturing fixtures and secured in place with the insulation layer 140.

Figure 1:
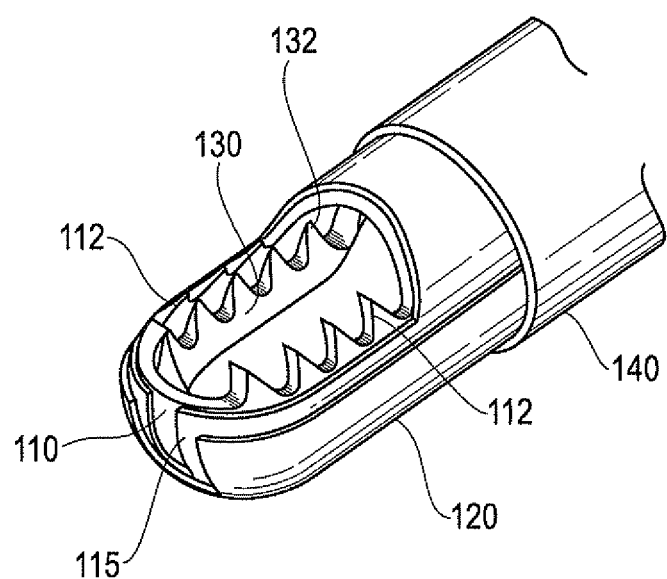
FIG. 1 is a perspective view of a known bipolar surgical cutting instrument.

The design embodied in FIGS. 7-10 is advantageous compared to the FIG. 1 design in that, by disposing each of the electrodes 70 and 80 in the same layer, it is easier for the surgeon to contact the electrodes with the tissue that is to be cauterized. The design of FIGS. 7-10 also makes it easy to place the electrodes 70 and 80 on opposite sides of the tissue that is to be treated, thereby easing the cauterizing procedure. Furthermore, the design of FIGS. 7-10 enables the spacing between the electrodes 70 and 80 to be adjusted (by varying the spacing between the electrodes 70 and 80, and also the width of the protrusion 65 if provided) to optimize the design for the desired tissue effect and time required for that effect as desired by the user.

If the outer tube 10 is made from an electrically insulative material, then it would not be necessary to provide the insulative layer 60 over the outer tube 10. It would, however, be preferable to provide the protrusion 65 on at least a portion of the outer tube 10 if the outer tube 10 is made from an electrically insulative material.

If the surgical instrument is a microdebrider having a cutting window at the distal end of the outer tube 10, as shown in FIGS. 7-10, an electrically insulative outer tube 10 must be made from a material that also could include the requisite cutting edge to form the cutting window. This could be achieved by treating at least the distal tip of a stainless steel cutting blade so that at least the distal tip becomes electrically insulative.

Figure 11:
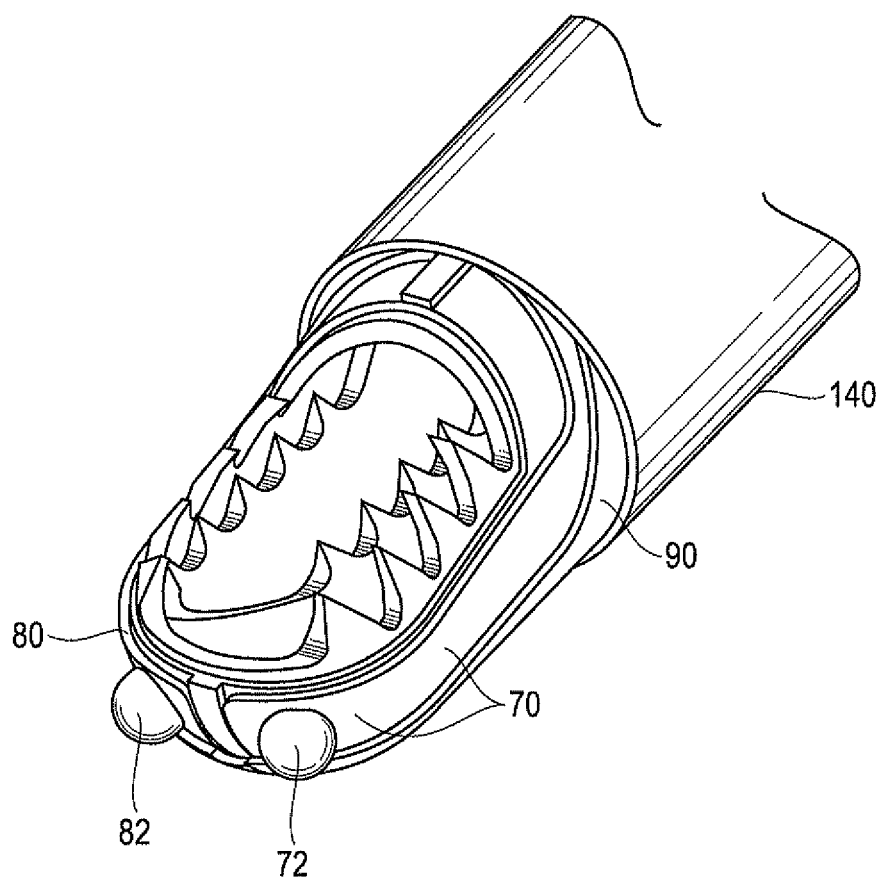
FIG. 11 is a perspective view of a modified version of the FIG. 7 embodiment.

FIG. 11 shows a modified embodiment in which each of the electrodes 70 and 80 includes a forward-facing projection such as a bump located at the distal end of the surgical instrument 8. In particular, electrode 70 includes distal bump 72, whereas electrode 80 includes distal bump 82. The bumps 72 and 82 make it even easier to engage the tissue that is to be subjected to coagulation. One or both of the electrodes 70, 80 can include one or more of the projections/bumps.

Figure 12:
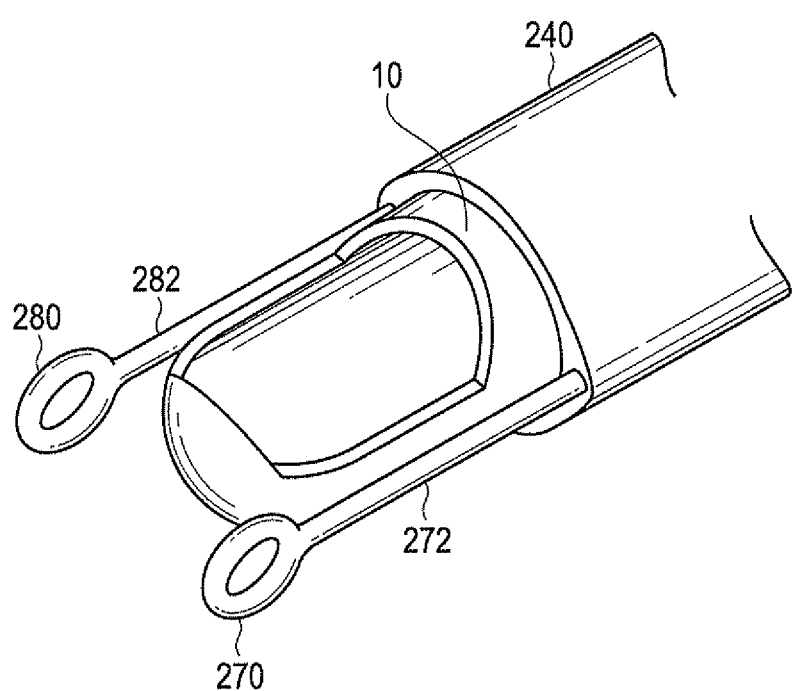
FIG. 12 is a perspective view of another bipolar surgical instrument.

FIG. 12 illustrates another embodiment that is less preferable than the embodiments of FIGS. 2-11. The FIG. 12 embodiment includes a relatively thick insulative sheath 240 through which wire electrodes 272 and 282 extend. The distal end of each wire electrode 272, 282 includes a ring-shaped electrode 270 and 280. The sheath 240 can be extruded and includes lumens through which the wire electrodes 272, 282 extend. The FIG. 12 embodiment is less preferred because the sheath 240 substantially increases the overall diameter of the surgical instrument 8. For example, in the FIG. 12 embodiment, the sheath 240 has a thickness of approximately 0.025 inch to 0.050 inch in the area of the electrodes in the sections where the wire electrodes 272 and 282 extend. On the other hand, each of the electrodes 70 and 80 in the embodiments of FIGS. 2-11 has a thickness of approximately 0.005 inch to 0.010 inch. In addition, the insulative layer 60, if needed, has a thickness of approximately 0.005 inch to 0.010 inch (except for the area of the protrusion 65, which has a thickness of approximately 0.010 inch to 0.015 inch). The insulative layer 90 has a thickness of approximately 0.005 inch to 0.010 inch.

The surgical instrument described above is intended for ear, nose and throat surgery. It will be appreciated, however, that the surgical instrument could be used at any surgical site located within the body of a patient where surgery is to be performed, including arthroscopic use, for example, on joints such as shoulders or knees. The surgical instrument is primarily intended for use with an endoscope, but also may be used in "open" procedures that allow a surgeon to view a surgical site. In such a case, the surgical instrument is inserted through a first incision, and the endoscope is inserted through a second incision. The distal ends of both the endoscope and the surgical instrument are positioned adjacent to the surgical site, and the surgeon can view the surgical site on a monitor attached to the endoscope.

In use, once the endoscope and surgical instrument have been positioned adjacent to the surgical site, saline is fed from the fluid source 22 via the inlet port 26 into passage 20 to the surgical site. The surgeon depresses the foot switch 12 to send a signal to a controller/generator 100 so that a radio frequency signal is supplied to the handpiece 2. The radio frequency signal is provided via one or both of the connections 70A and 70B. Current thus flows between the electrodes 70 and 80 and the tissue disposed therebetween so as to coagulate the tissue.

In addition, as commanded by the surgeon, the inner cutting tube 9 rotates within the outer cutting tube 10 while suction is supplied from suction source 28 in order to shave and remove tissue from the surgical site.

In accordance with one example, the signal supplied to the electrodes could be a nominal 350 kHz radio frequency signal operated at a 35 watt setting in coagulation mode. The signal could be 10-50 watts through a rated load up to 100 Ohm.

The invention has been described with reference to a rotary shaver, but it will be appreciated by those skilled in the art that the invention can equally be employed with other surgical cutting devices, such as burrs, drills, etc. The inner cutting blade could reciprocate axially instead of rotating about the longitudinal axis in order to effect cutting/shaving. The cutting window or opening of the outer cutting blade also could be provided at, or extend to, the distal end (tip) of the outer cutting blade rather than being sideward-facing. Furthermore, the invention is applicable to a variety of hollow tubular members that are inserted into the body where coagulation is required or desired. That is, the tubular member having the electrodes could be used for procedures other than cutting.

Furthermore, when the outer tube 10 is electrically conductive, it could be used as an electrode in addition to one or both of the electrodes 70 and 80. In such an apparatus, a signal appropriate for vaporizing tissue can be supplied to the hollow tubular member defining the outer tube 10 (using the portion of the outer tube 10 adjacent to the window 40 as an active electrode) while one or both of the electrodes 70/80 can be used as a return electrode.

In the illustrated embodiment, the inner and outer tubes 9 and 10 are straight. However, the surgical instrument 8 can have one or more bends in it such that it is not straight. In such an arrangement, the inner tube 9 would be flexible. Flexible hollow cutting blades are known and used with curved cutting instruments. See, for example, U.S. Pat. No. 4,646,738, the disclosure of which is incorporated herein by reference in its entirety, and see, for example, U.S. Pat. No. 5,707,350, the disclosure of which is incorporated herein by reference in its entirety.

The illustrated exemplary embodiments of the surgical tool as set forth above are intended to be illustrative and not limiting. Various changes may be made without departing from the spirit and scope of the invention.

What is claimed is:

1. A surgical instrument comprising:
   a hollow tubular member having a closed distal working end, a proximal end and an outer surface, with an opening in a side wall at or adjacent the distal working end;
   a first electrical insulation layer disposed on at least part of the outer surface of the hollow tubular member;
   a first electrode disposed on an outer surface of the first electrical insulation layer, the first electrode being electrically isolated from the hollow tubular member by the first electrical insulation layer; and
   a second electrode disposed on the outer surface of the first electrical insulation layer, the second electrode being electrically isolated from the hollow tubular member by the first electrical insulation layer,
   wherein (i) the first and second electrodes are electrically isolated from each other, (ii) the first electrode includes a first active segment, (iii) the second electrode includes a second active segment, and (iv) the first and second active segments are disposed respectively on opposite sides of the opening in the side wall of the hollow tubular member within about 3.0 mm of the opening in the side wall of the hollow tubular member so that the opening is located between the first and second active segments and a line that is perpendicular to and passes through a longitudinal axis of the hollow tubular member intersects the first and second active segments on the opposite sides of the opening.

2. The surgical instrument according to claim 1, wherein the first and second active segments are disposed respectively within 1.0 mm of the opening in the side wall of the hollow tubular member.

3. The surgical instrument according to claim 1, wherein one or both of the first and second active segments are further disposed at least partially into a segment of the closed distal working end of the hollow tubular member.

4. The surgical instrument according to claim 2, wherein one or both of the first and second active segments are further disposed at least partially into a segment of the closed distal working end of the hollow tubular member.

5. The surgical instrument according to claim 1, further comprising a rotatable cutting member disposed within the hollow tubular member, the rotatable cutting member being rotatable relative to the hollow tubular member.

6. The surgical instrument according to claim 1, further comprising a second electrical insulation layer disposed at least partially over the outer surface of the hollow tubular member, portions of the first and second electrodes, or both.

7. The surgical instrument according to claim 6, wherein the first electrical insulation layer, the second electrical insulation layer, or both include geometric features adapted to isolate the first and second electrodes from each other.

8. The surgical instrument according to claim 6, further comprising an outer sheath that is disposed at least partially over the second electrical insulation layer.

9. The surgical instrument according to claim 1, wherein the first active segment, the second active segment, or both include a forward facing projection.

10. The surgical instrument according to claim 1, wherein at least a portion of the side wall at the opening is electrically conductive and can function as an active electrode segment.

11. A surgical instrument comprising:
an electrically conductive hollow tubular member having a closed distal working end, a proximal end and an outer surface, with an opening in a side wall at or adjacent the distal working end;
a rotatable cutting member disposed within the electrically conductive hollow tubular member, the rotatable cutting member being rotatable relative to the electrically conductive hollow tubular member;
a first electrical insulation layer disposed on at least part of the outer surface of the electrically conductive hollow tubular member;
a first electrode disposed on an outer surface of the first electrical insulation layer; and
a second electrode disposed on the outer surface of the first electrical insulation layer,
wherein (i) the first and second electrodes are electrically isolated from each other, (ii) the first electrode includes a first active segment, (iii) the second electrode includes a second active segment, and (iv) when the opening in the side wall of the electrically conductive hollow tubular member is viewed from a position above the opening, the first and second active segments are disposed respectively along linear portions of the electrically conductive hollow tubular member on opposite sides of the opening in the side wall of the electrically conductive hollow tubular member within about 2.0 mm of the opening in the side wall of the electrically conductive hollow tubular member so that when viewed from the position above the opening, the opening is located between the first and second active segments.

12. The surgical instrument according to claim 11, further comprising a second electrical insulation layer disposed at least partially over the outer surface of the electrically conductive hollow tubular member, portions of the first and second electrodes, or both.

13. The surgical instrument according to claim 12, wherein the first electrical insulation layer, the second electrical insulation layer, or both include geometric features adapted to isolate the first and second electrodes from each other.

14. The surgical instrument according to claim 12, further comprising an outer sheath that is disposed at least partially over the second electrical insulation layer.

15. The surgical instrument according to claim 11, wherein the first active segment, the second active segment, or both include a forward facing projection.

16. The surgical instrument according to claim 11, wherein at least a portion of the side wall at the opening can function as an active electrode segment.

17. A surgical instrument comprising:
a hollow tubular member having a closed distal working end, a proximal end and an outer surface, with an opening in a side wall at or adjacent the distal working end;
a first electrical insulation layer disposed on at least part of the outer surface of the hollow tubular member;
a first electrode disposed on an outer surface of the first electrical insulation layer, the first electrode being electrically isolated from the hollow tubular member by the first electrical insulation layer; and
a second electrode disposed on the outer surface of the first electrical insulation layer, the second electrode being electrically isolated from the hollow tubular member by the first electrical insulation layer,
wherein (i) the first and second electrodes are electrically isolated from each other, (ii) the first electrode includes a first active segment, (iii) the second electrode includes a second active segment, and (iv) the first and second active segments extend in a direction that is parallel to a longitudinal axis of the hollow tubular member and are disposed respectively on opposite sides of the opening in the side wall of the hollow tubular member relative to the longitudinal axis so that the opening is located between portions of the first and second active segments that extend in the direction that is parallel to the longitudinal axis of the hollow tubular member, and
wherein edges of the first and second electrodes located adjacent to the opening are recessed from an edge of the opening so that a portion of the first electrical insulation layer is exposed between the edge of the opening and the edges of the first and second electrodes.

18. The surgical instrument according to claim 17, wherein the edges of the first and second electrodes located adjacent to the opening are recessed within about 3.0 mm of the opening in the side wall of the hollow tubular member.

19. The surgical instrument according to claim 18, wherein the edges of the first and second electrodes located adjacent to the opening are recessed from the edge of the opening by no more than 2.0 mm.

20. The surgical instrument according to claim 18, wherein the edges of the first and second electrodes located adjacent to the opening are recessed from the edge of the opening by 0.5 mm to 1.0 mm.

* * * * *